United States Patent [19]
Janisiwicz et al.

[11] Patent Number: 5,270,059
[45] Date of Patent: Dec. 14, 1993

[54] METHOD AND PREPARATION FOR INHIBITING MOLD GROWTH ON POME FRUIT

[75] Inventors: Wojciech J. Janisiwicz, Frederick; Robert H. Bors, New Carrollton, both of Md.

[73] Assignee: The United States of America as represented by the United States Department of Agriculture, Washington, D.C.

[21] Appl. No.: 930,632

[22] Filed: Aug. 17, 1992

[51] Int. Cl.$^5$ .................. A01N 63/00; A61K 37/00; C12N 1/20; C12N 1/16

[52] U.S. Cl. .................. 424/935; 424/93 N; 435/255.1; 435/253.3; 435/252.4

[58] Field of Search ............ 424/935, 93 N; 435/255, 435/253.3, 252.4

[56] References Cited

U.S. PATENT DOCUMENTS

| | | | |
|---|---|---|---|
| 3,891,505 | 6/1975 | Kotiuszko et al. | 435/909 |
| 3,976,546 | 8/1976 | Smith et al. | 435/197 |
| 4,226,719 | 10/1980 | Aida et al. | 435/411 |
| 4,950,472 | 8/1990 | Janisiewicz | 435/253.3 |

OTHER PUBLICATIONS

*ATCC Catalogue of Yeasts* 18th Ed., 1990, p. 91.

*Primary Examiner*—David M. Naff
*Assistant Examiner*—Jeffrey J. Sevigny
*Attorney, Agent, or Firm*—Hamilton, Brook, Smith & Reynolds

[57] ABSTRACT

A method and preparation are disclosed for inhibiting the growth of mold on a pome fruit. The method includes exposing the pome fruit to a preparation which includes a sufficient concentration of *Sporobolomyces roseus* to significantly inhibit the growth of the mold on the fruit. In particular, the mold is a blue-mold or a gray-mold. The preparation includes *Sporobolomyces roseus* having a concentration which is sufficient to significantly inhibit the growth of the mold on the fruit. The preparation can further include an additional component which can significantly inhibit the growth of the mold. An example of a suitable additional component is *Pseudomonas syringae* bacteria.

16 Claims, 6 Drawing Sheets

METHOD AND PREPARATION FOR INHIBITING MOLD GROWTH ON POME FRUIT

BACKGROUND OF THE INVENTION

Many fruits suffer from postharvest diseases which are caused by pathogens, such as fungi, that can cause rot and other forms of decay during handling and storage. Often, infection by pathogens is initiated through injuries made at harvest through cut stems, etc. or through mechanical wounds to the surface of the fruit during processing. This decay on harvested fruit can cause substantial economical losses to the fruit industry each year.

Pome fruits, which include apples and pears, are examples of fruits that are vulnerable to infection by postharvest diseases. In particular, pome fruits are attached by blue-mold and gray-mold, which are present on the fruits at harvest and then grow during storage and shipping, causing severe decay.

Past attempts to control postharvest diseases have included, for example, the treatment of the fruits with chemicals. However, many chemicals which have been in long-time use are now ineffective due to the increasing number of chemical-resistant strains of pathogens associated with postharvest diseases. Further, many chemicals have been recently recognized as hazardous to humans and the environment.

Biological control of postharvest diseases is an alternative to chemical control of plant pathogens. However, few biocontrol products are commercially available. Further, biocontrol agents, such as fungicides, are increasingly susceptible to multiplying numbers of fungicide-tolerant strains of pathogens associated with postharvest diseases. Furthermore, as with chemicals, there is a need for fungicides that are safe to humans and the environment.

Thus, a need exists for a method and composition for controlling the growth of mold on postharvest pome fruits which overcome or minimize the above mentioned problems.

SUMMARY OF THE INVENTION

The present invention relates to a method and a preparation for inhibiting the growth of mold on postharvest pome fruits. The method includes exposing the pome fruit to a preparation which includes a sufficient concentration of *Sporobolomyces roseus* yeast to significantly inhibit the growth of the mold on the fruit. The preparation includes *Sporobolomyces roseus* in a concentration which is sufficient to significantly inhibit the growth of the mold. In a preferred embodiment, a second component is included, which can significantly inhibit the growth of mold on the fruit, such as *Pseudomonas syringae* bacteria.

This invention has many advantages. For example, *Sporobolomyces roseus* occurs naturally and grows well under conditions typically encountered in postharvest storage. The preparation, which includes the yeast, is easy to apply to the surface of fruit and is safe to handle. Also, *Sporobolomyces roseus* exhibits good survivability and growth of the agent under conditions, such as temperature and humidity, which are typically encountered during postharvest treatment and storage. Further, *Sporobolomyces roseus* colonize wound surfaces very effectively.

DETAILED DESCRIPTION OF THE INVENTION

The above features and other details of the composition and method of this invention for controlling the growth of mold on postharvest pome fruits will now be more particularly described with relevance to the accompanying drawings and pointed out in the claims. It will be understood that the particular embodiments of the invention are shown by way of illustration and not as limitations of the invention. The principle feature of this invention can be employed in various embodiments without departing from the scope of the invention.

The invention generally includes a method and a preparation for significantly inhibiting the growth of mold on postharvest pome fruits. The method includes exposing the pome fruit to a preparation which includes a sufficient concentration of *Sporobolomyces roseus* to significantly inhibit the growth of the mold on the fruit. The preparation includes *Sporobolomyces roseus* in a concentration which is sufficient to significantly inhibit the growth of mold on the fruit.

Suitable fruits for use with this invention include, for example, pome fruits. Pome fruits typically have a fleshy outer layer and a central core with seeds, which are enclosed in a capsule. Examples of suitable pome fruits include, but are not limited to, apples, pears, pomegranates, quinces and the like.

Postharvest diseases, which commonly infect pome fruits, include blue-mold (*Penicillium expansum*) and gray-mold (*Botrytis cinerea*). Often, infection is initiated by injuries made at harvest or by mechanical wounds to the surface of the fruit during processing.

The preparation is formed by first isolating *Sporobolomyces roseus* Kluyver and van Neil yeast (isolate FS-43-238). This yeast was identified by Contraalbureau Voop Schimmelcultures, Netherlands. The yeast exhibits a pink color. In one embodiment, the yeast is isolated from an apple or pear surface by repeatedly rinsing the surface with a suitable aqueous buffer, i.e. a phosphate buffer.

*Sporobolomyces roseus* is then cultured in a suitable shake flask. Alternatively, the yeast can be cultured in a fermentation tank. The yeast is plated and cultured in a nutritionally-rich medium which is sufficient to support the growth of the organism. A preferred medium includes nutrient yeast dextrose broth (NYDB) or nutrient yeast dextrose agar (NYDA). The yeast is cultured under aerobic conditions at a suitable temperature, such as a temperature in the range of between about 1° and 28° C. The preferred temperature is about 24° C. The pH of the nutrient media is in the range of between about 2.8 and 9.0. The period of incubation required for the yeast to reach a stationary phase is generally between about 24 and 36 hours.

Figure 1:
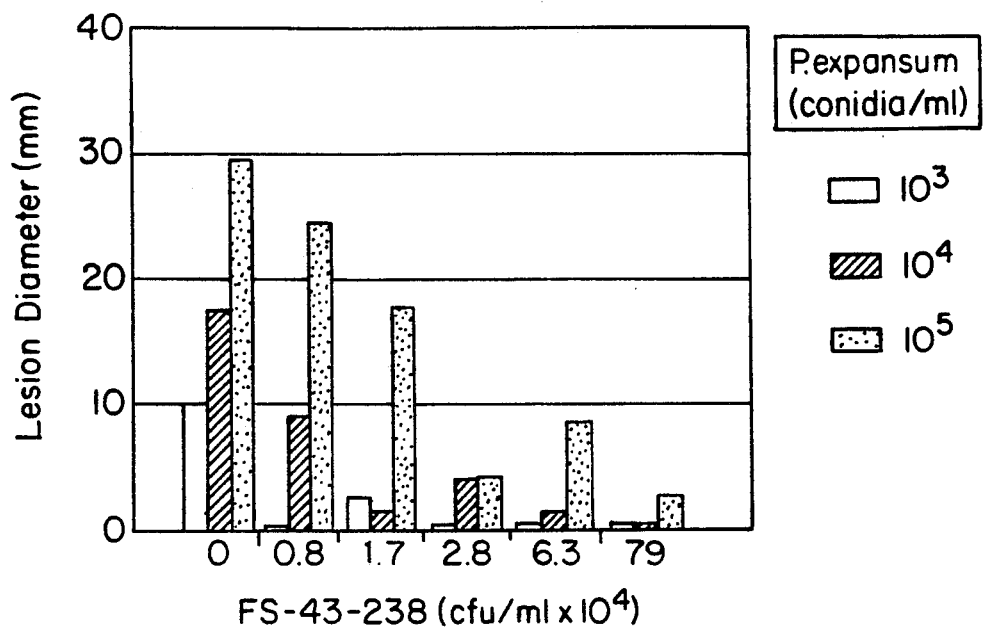
FIG. 1 is a histogram of the size of lesion development on Golden Delicious apples inoculated with blue-mold and which were treated with various preparations according to the method of the invention.

The cultured yeast is then harvested, such as by centrifugation or filtration, and then stored at a suitable temperature, such as a temperature of about 5° C. Thereafter, the yeast is suspended in a suitable medium, such as water, to form the preparation. The concentration of the *Sporobolomyces roseus* is sufficient to significantly inhibit the development of the mold on pome fruits. Significant inhibition is understood to be a concentration which causes an observable decrease in growth as compared to growth on a control sample fruit. An example of this is seen in FIG. 1, which displays the size of lesion development on Golden Delicious apples inoculated with blue-mold (*Penicillium expansum*) and which were treated with various concentrations of *Sporobolomyces roseus*, as compared to a control sample. The difference in the size of lesions between the control sample (30 mm) having $10^5$ conidia per milliliter of *Penicillium expansum* and treated with zero colony forming units (cfu)/ml of *Sporobolomyces roseus*, and a test sample (25 mm) having $10^5$ conidia per milliliter of *Penicillium expansum* and treated with $0.8 \times 10^4$ cfu/ml of *Sporobolomyces roseus* is considered significantly inhibited. In one embodiment, *Sporobolomyces roseus* has a concentration in an aqueous suspension of the preparation in the range of between about $10^3$ cfu/ml and $10^6$ cfu/ml. In a preferred embodiment, *Sporobolomyces roseus* has a concentration in the range of between about 8,000 cfu/ml and 790,000 cfu/ml.

More than one component that can inhibit mold growth included in the preparation to control the growth of mold on pome fruits by the method of the invention. For example, *Sporobolomyces roseus* can be combined with a second component *Pseudomonas syringae* (isolate L-59-66), identified by Contraalbureau Voop Schimmelcultures. In a particularly preferred embodiment, a suspension of two agents has a volume ratio of 40:60 of a *Sporobolomyces roseus* aqueous suspension having a concentration of about $6.3 \times 10^4$ cfu/ml and a *Pseudomonas syringae* aqueous suspension having a concentration of about $7 \times 10^8$ cfu/ml, respectively.

The preparation is the applied to the surface of the fruit by a suitable technique. Examples of suitable techniques include spraying, dipping or brushing. The suspensions can be applied before or after harvest of the fruit. Preferably, the treatments are applied after harvest and prior to storage. The preparation can contain additives to further increase the effectiveness of application of the preparation. Examples of suitable additives include surfactants and antioxidants.

It is believed that the preparation of the invention, when applied to a pome fruit significantly inhibits the growth of mold by several mechanisms, including reducing the nutrient base for the mold on the fruit.

The following are examples of various embodiments of the method and the preparation for inhibiting the growth of mold on pome fruits.

EXAMPLE 1

Golden Delicious apples were obtained from commercial orchards using standard cultivation practices. The apples were used within three months of having been harvested and which had been stored at 1° C. during the time between harvesting and testing. The apples had an average firmness of about 41.1 Newtons (N), a soluble solids concentration of 11.5 and a stage six on a one to six scale for a starch iodine test.

The pathogen for blue-mold, *Penicillium expansum*, was isolated from decayed apples after a few months in storage. The isolate produced large lesions when inoculated to untreated apples. The fungus was maintained on potato dextrose agar (PDA). The inocula consisting of aqueous conidial suspensions of $10^3$, $10^4$ and $10^5$ conidia per milliliter were prepared from 10 day old culture of *Penicillium expansum*.

The antagonistic yeast, *Sporobolomyces roseus* isolate FS-43-238 was isolated by the method described above. The yeast was maintained on NYDA at 5° C. prior to preparation of the suspension for application to the apples.

For the experiments on the apples, the yeast cell cultures were grown in 250 ml Erlenmeyer flasks with 50 ml NYDB on a rotary shaker at 150 rpm for 36 hours at 24° C. The resulting yeast cells were harvested by centrifugation at 7,000 rpm for 10 minutes. The pellet of cells was resuspended in water, and the concentration of cells in the suspension was adjusted with a PC 900 Colorimeter fiber optic probe (Brinkman Instruments, Westbury, N.Y.) according to a standard curve.

Immediately before treatment, the apples were wounded with a sharp instrument, and two blocks of tissue, 3 mm ×3 mm ×3 mm in size, were removed along the stem-calyx axis approximately 2 cm apart. The apples were placed on fruit trays in plastic containers. A series of apple wounds were inoculated with 25 μl of antagonist suspension having concentrations of zero, 0.8, 1.7, 2.8, 6.3 and $79 \times 10^4$ cfu/ml.

Within thirty minutes of application of the antagonist, the apples were inoculated with 20 µl of $10^3$ or $10^4$ or $10^5$ conidial per milliliter suspension of *Pencillium expansum*. The inoculated apples were stored at 22° C. for seven days.

Three replications per treatment were made. Each replication consisted of three fruit (six wounds). Each replication of the concentration of the pathogen was arranged in two boxes and consisted of a single block. The blocks were randomly distributed. At the end of seven days, the diameters of the lesions, which developed from the wounds, were measured perpendicular to the stem-calyx axes.

In FIG. 1, the lesion development on the wounded Golden Delicious apples that were treated with *Sporobolomyces roseus* (isolate FS-43-238) and challenged into various concentrations of conidia of *Penicillium expansum* is shown in a histogram. Treatment of the wounded apples with *Sporobolomyces roseus* reduced or completely eliminated lesions that developed from *Penicillium expansum*. No lesions developed on the Golden Delicious apples that were protected with 790,000 cfu/ml of *Sporobolomyces roseus* and inoculated with $10^3$ and $10^4$ conidia of *Penicillium expansum*.

Figure 2:
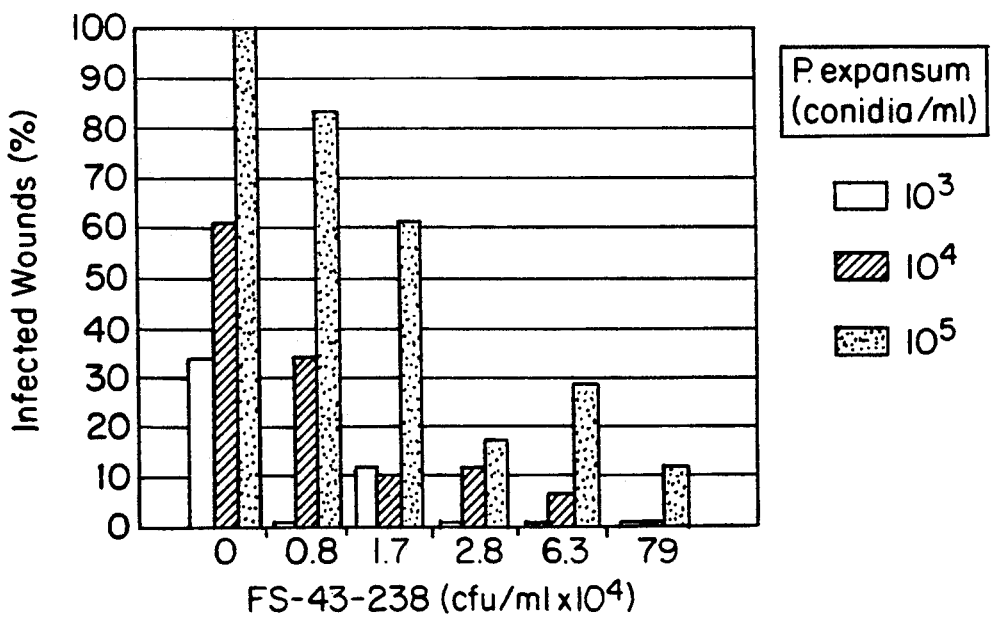
FIG. 2 is a histogram of the percentage of wounds on Golden Delicious apples inoculated with blue-mold and which thereafter became infected, following treatment with various preparations according to the method of the invention.

In FIG. 2, the percentage of wounds infected on wounded Golden Delicious apples that were treated with the various concentrations of *Sporobolomyces roseus* and challenged with various concentrations of conidia of *Penicillium expansum* is shown. The percentage of wounds decreased with increased antagonist concentrations for all tested concentrations of pathogens.

EXAMPLE 2

The same procedure was followed as in Example 1, except Anjou pears were tested instead of Golden Delicious apples. The pears were also obtained from commercial orchards using standard cultivation practices. The pears were used within three months from having been harvested and were stored at 1° C. during the time between harvesting and testing. At the beginning of the experiment, the pears had a firmness of 66.7 N. The inoculated pears were stored at 22° C. for only five days instead of seven days for the apples.

Figure 3:
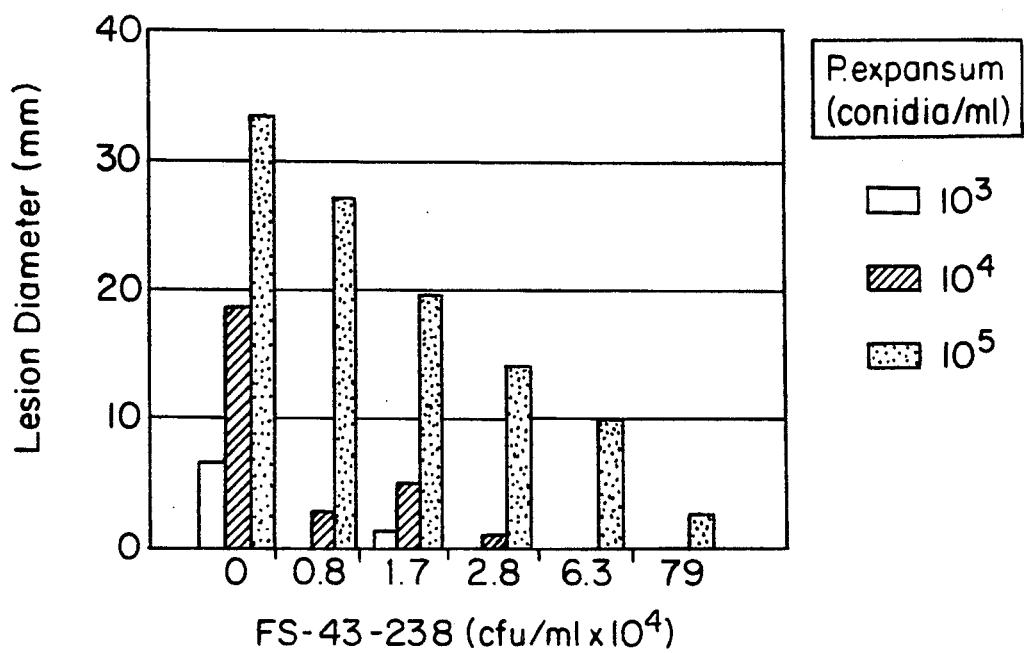
FIG. 3 is a histogram of the size of lesion development on Anjou pears inoculated with blue-mold and which were treated with various preparations according to the method of the invention.

As shown in FIG. 3, the wounded pears that were treated with *Sporobolomyces roseus* reduced or completely prevented lesions from developing with *Penicillium expansum*. As concentrations of the antagonist increased, lesion-size decreased at all concentrations of *Penicillium expansum*. Further, no lesions developed on the Anjou pears that were inoculated with the two highest concentrations of *Sporobolomyces roseus* and that were inoculated with $10^3$ and $10^4$ conidia of *Penicillium expansum*.

Figure 4:
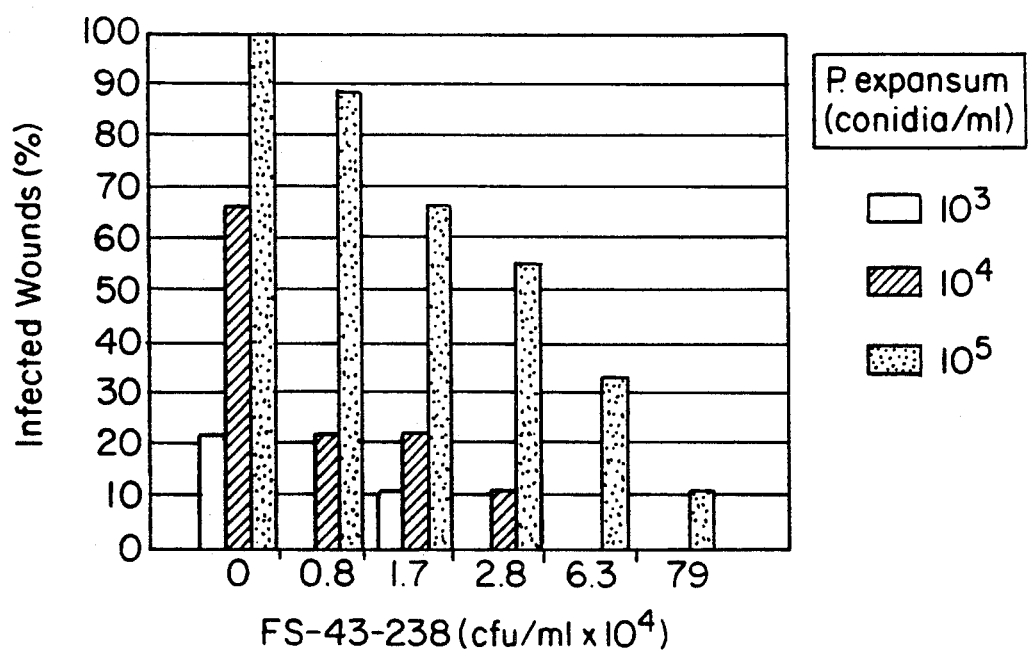
FIG. 4 is a histogram of the percentage of wounds on Anjou pears inoculated with blue-mold and which thereafter became infected, following treatment with various preparations according to the method of the invention.

In FIG. 4, the percentage of wounds infected on the wounded Anjou pears that were treated with various concentrations of *Sporobolomyces roseus* and challenged with various concentrations of conidia of *Penicillium expansum* is shown. The percentage of wounds decreased with increased antagonist concentrations for all tested concentrations of pathogens.

EXAMPLE 3

The same procedure was followed as in Example 1 except the Golden Delicious apple wounds were inoculated with the pathogen for gray-mold, *Botrytis cinerea*.

*Botrytis cinerea* was isolated from decayed apples after a few months in storage. The fungus was maintained on PDA. The inocula consisting of aqueous conidial suspensions of $10^3$, $10^4$ and $10^5$ conidia per milliliter were prepared from 4 day old cultures of *Botrytis cinerea*.

Figure 5:
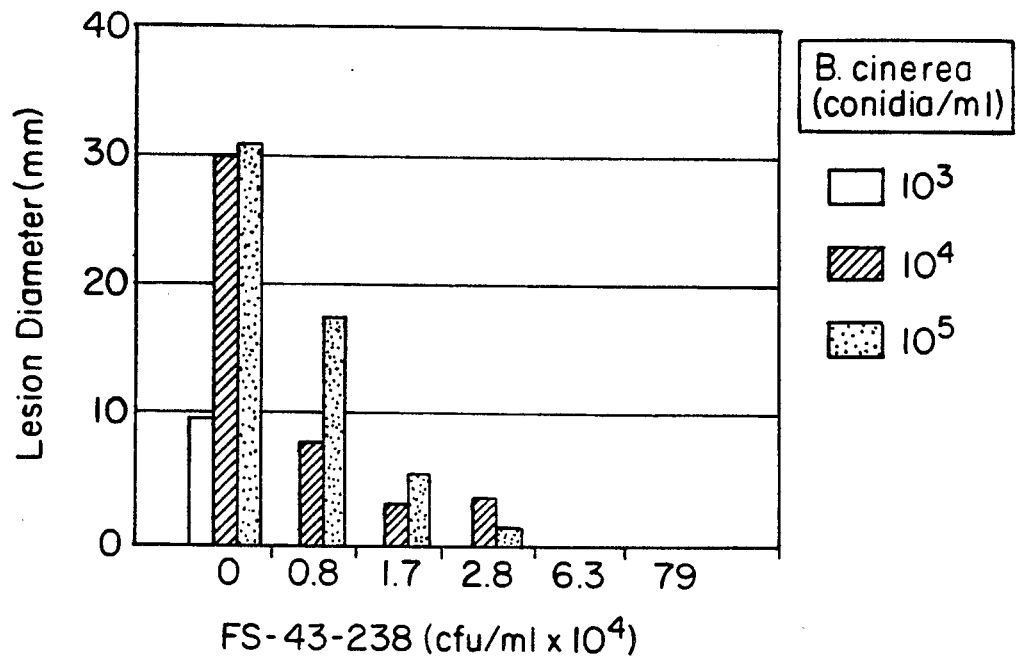
FIG. 5 is a histogram of the size of lesion development on Golden Delicious apples inoculated with gray-mold and which were treated with various preparations according to the method of the invention.

In FIG. 5, the lesion development on the wounded Golden Delicious apples that were treated with *Sporobolomyces roseus* and challenged into various concentrations of *Botrytis cinerea* is shown in a histogram. Treatment of the wounded apples with *Sporobolomyces roseus* effectively reduced or completely eliminated lesions that developed from *Botrytis cinerea*. No lesions developed on the apples that were protected with $6.3 \times 10^4$ and $79 \times 10^4$ cfu/ml of *Sporobolomyces roseus* and inoculated with $10^3$, $10^4$ and $10^5$ cfu/ml of *Botrytis cinerea*.

Figure 6:
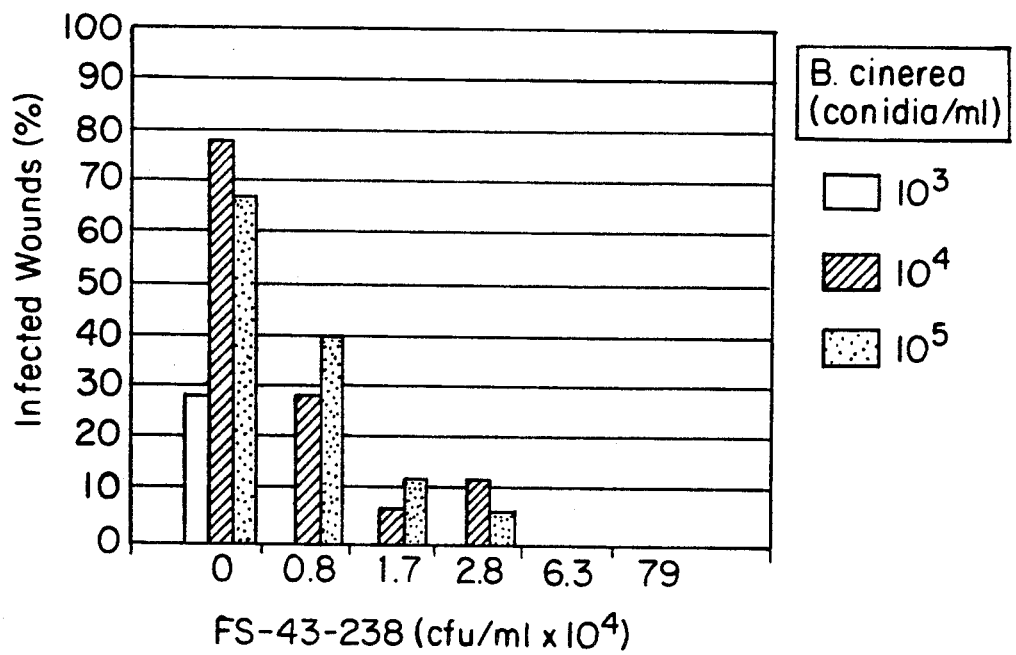
FIG. 6 is a histogram of the percentage of wounds on Golden Delicious apples inoculated with gray-mold and which thereafter became infected, following treatment with various preparations according to the method of the invention.

In FIG. 6, the percentage of wounds infected on wounded apples that were treated with the various concentrations of *Sporobolomyces roseus* and challenged with various concentrations of conidia of *Botrytis cinerea* is shown. Less than ten percent of the wounds and in some cases none of the wounds developed lesions where the concentration of *Sporobolomyces roseus* were 17,000 cfu/ml or greater for all concentrations of *Botrytis cinerea* tested.

EXAMPLE 4

The same procedure was followed as in Example 2 except the wounded Anjou pears were inoculated with the pathogen for gray-mold, *Botrytis cinerea*. *Botrytis cinerea* was isolated by the same method as described in Example 3.

Figure 7:
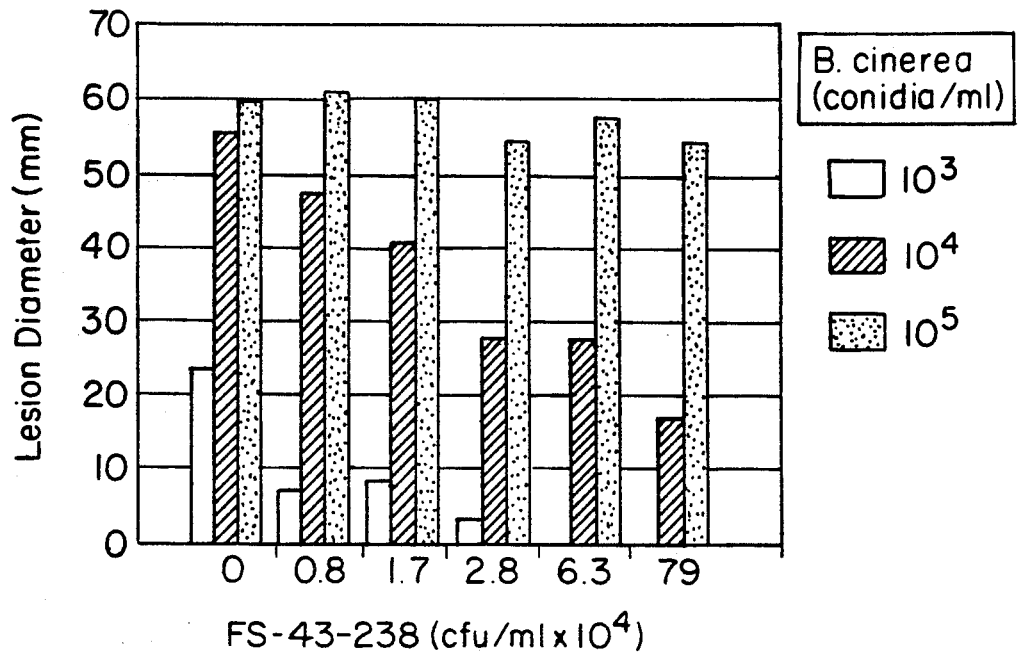
FIG. 7 is a histogram of the size of lesion development on Anjou pears inoculated with gray-mold and which were treated with various preparations according to the method of the invention.

As shown in the histogram in FIG. 7, the lesion development on wounded Anjou pears that were treated with *Sporobolomyces roseus* and challenged into various concentrations of *Botrytis cinerea* is illustrated. No lesions developed on the pears that were protected with the two highest concentrations of *Sporobolomyces roseus* and inoculated with $10^3$ conidia/ml of *Botrytis cinerea*.

Figure 8:
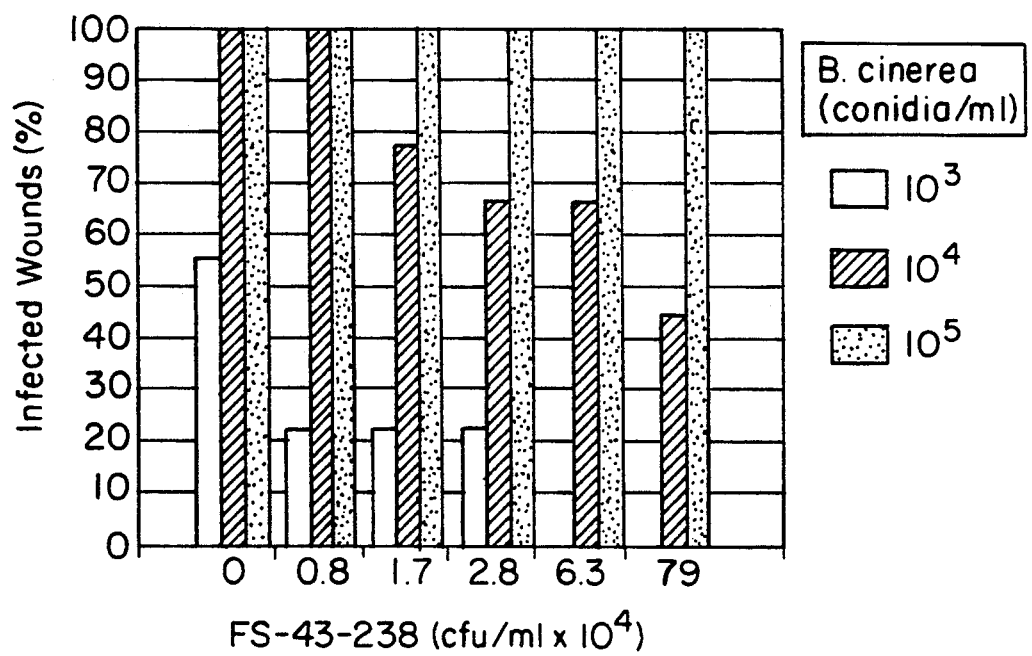
FIG. 8 is a histogram of the percentage of wounds on Anjou pears inoculated with gray-mold and which thereafter became infected, following treatment with various preparations according to the method of the invention.

FIG. 8 illustrates the percentage of wounds infected on wounded pears that were treated with various concentrations of *Sporobolomyces roseus*. For the wounds inoculated with $10^3$ conidia/ml of *Botrytis cinerea*, the infection rates were about 20 percent or less.

EXAMPLE 5

A suspension of *Sporobolomyces roseus* was formed at a concentration of $6.3 \times 10^4$ cfu/ml by the method described above. A second suspension was also formed with bacterial agent *Pseudomonas syringae* having a concentration of $1.7 \times 10^8$ cfu/ml. *Pseudomonas syringae* was isolated from apple leaf surfaces in a procedure similar to the method described above for *Sporobolomyces roseus*.

The two suspensions were mixed in volumetric in ratios of 100:0, 80:20, 60:40, 50:50, 40:60, 20:80 and 0:100. The mixtures were treated on the wounded apples, as described in Example 1, within a half hour of being challenged with *Penicillium expansum* at $10^4$ conidia/ml. The fruit was incubated for seven days at 22° C. similarly to the other tests on fruit with *Sporobolomyces roseus* alone.

The diameters of lesions developing from wounds were measured. Each treatment was made on six fruit. The treatments were replicated three times. The treatments were arranged as a completely random block design.

Figure 9:
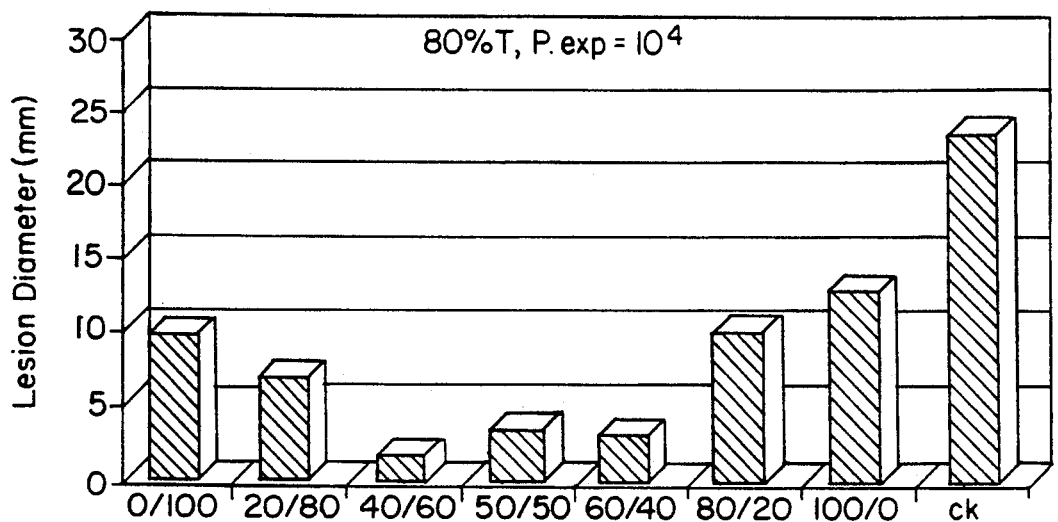
FIG. 9 is a histogram of the size of lesion development on Golden Delicious apples that were inoculated with blue-mold and which were treated with two antagonists of various preparations according to the method of the invention.
Figure 10:
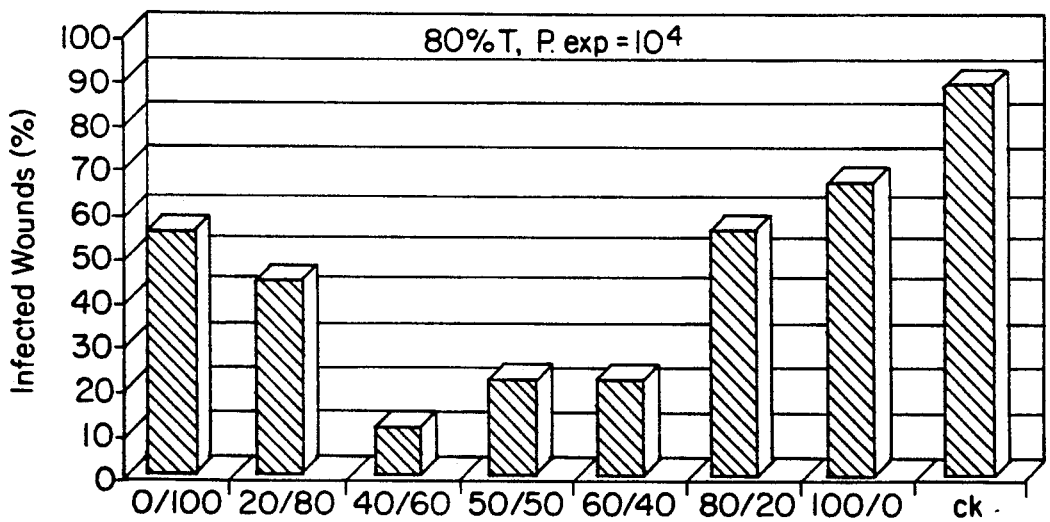
FIG. 10 is a histogram of the percentage of wounds infected on Golden Delicious apples that were inoculated with blue-mold and which thereafter became infected, following treatment with two antagonists of various preparations according to the method of the invention.

Mixtures of the antagonistic yeast and bacterium were more effective in controlling blue-mold on ripe Golden Delicious apples than either of the antagonist alone. As shown in FIG. 9, the lesions were the smallest in the 40% *Penicillium expansum* and 60% *Sporobolomyces roseus* mixture having an average size of about 2 mm. FIG. 10 illustrates that only ten percent of the wounds were infected on apples that were treated with a mixture of 40% bacterium and 60% yeast antagonist. However, apples that were treated with either of the antagonists alone developed infections on more than 50% of the wounds.

EXAMPLE 6

In order to evaluate the survivability of the antagonist on fruit, Golden Delicious apples were wounded as described in Example 1 except only one wound was made per fruit. Each wound was inoculated with 25 µl of an aqueous suspension of *Sporobolomyces roseus* at $2 \times 10^4$ cfu/ml. One set of apples was placed on fruit trays in plastic boxes and stored at 18° C. for 19 days. A second set was stored at 1° C. for 35 days.

Figure 11:
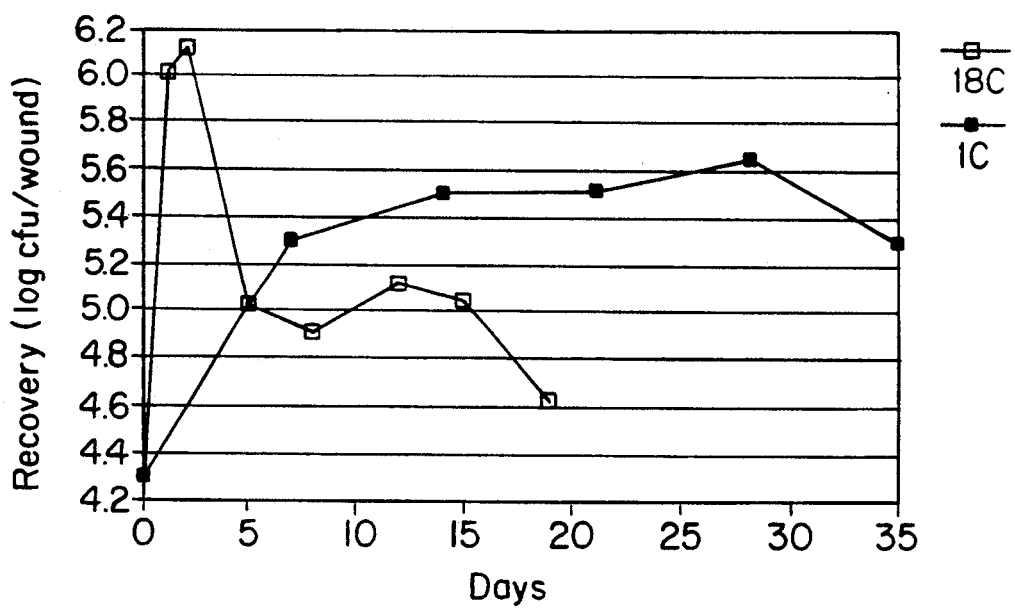
FIG. 11 is a plot of the recovery of an antagonist on Golden Delicious apples that were treated with the antagonist and then stored at 1° and 18° C.

For both sets of apples as shown in FIG. 11, the population of *Sporobolomyces roseus* increased within the first two days of storage. The population for the apples stored at 18° C. declined after the second day, but it was still greater than at the beginning of the storage. The population of antagonist increased by one order of magnitude after five days of storage and stabilized at this level over the next thirty days. These high levels indicated that the likelihood of *Sporobolomyces roseus* surviving was well enough that it would be an effective antagonist over an extended period of time.

EQUIVALENTS

Those skilled in the art will recognize, or be able to ascertain using no more than routine experimentation, many equivalents to the specific embodiments of the invention described specifically herein. Such equivalents are intended to be encompassed in the scope of the claims.

We claim:

1. A method for inhibiting the growth of a mold on a pome fruit, comprising the step of applying to the pome fruit a preparation comprising a sufficient concentration of *Sporobolomyces roseus* to inhibit the growth of the mold.

2. The method of claim 1 wherein the mold is blue-mold.

3. The method of claim 2 wherein the blue-mold is *Penicillium expansum*.

4. The method of claim 1 wherein the mold is gray-mold.

5. The method of claim 4 wherein the gray-mold is *Botrytis cinerea*.

6. The method of claim 1 wherein the pome fruit is apples or pears.

7. The method of claim 6 wherein the preparation further comprises *Pseudomonas syringae* bacteria which is in a concentration in the range of up to about $10^9$ cfu per milliliter and wherein the concentration of *Sporobolomyces roseus* is in the range of between about $10^3$ and $10^6$ cfu per milliliter.

8. The method of claim 7 wherein the preparation is an aqueous suspension.

9. A method for inhibiting the growth of a blue-mold or a gray-mold on a pome fruit, comprising the step of applying to the pome fruit a preparation comprising a sufficient concentration of *Sporobolomyces roseus* to inhibit the growth of the mold.

10. The method of claim 9 wherein the blue-mold is *Penicillium expansum*.

11. The method of claim 10 wherein the gray-mold is *Botrytis cinerea*.

12. The method of claim 9 wherein the pome fruit is an apple or a pear.

13. The method of claim 12 wherein the preparation further comprises *Pseudomonas syringae* present in a concentration of in the range of up to $10^9$ cfu per milliliter and wherein the concentration of *Sporobolomyces roseus* is in the range of between about $10^3$ and $10^6$ cfu per milliliter.

14. A composition for inhibiting the growth of a blue-mold or a gray-mold on a pome fruit, said composition prepared by:
  a) isolating a *Sporobolomyces roseus* yeast;
  b) culturing the *Sporobolomyces roseus*;
  c) suspending the *Sporobolomyces roseus* in a medium to form a first suspension having a sufficient concentration of *Sporobolomyces roseus* in the range of between about $10^3$ and $10^6$ cfu per milliliter;
  d) isolating *Pseudomonas syringae* bacterium;
  e) culturing the *Pseudomonas syringae*;
  f) suspending the *Pseudomonas syringae* in a medium to form a second suspension having a concentration in the range of up to about $10^9$ cfu per milliliter of the *Pseudomonas syringae*; and
  g) combining the first suspension and second suspension to form a composition.

15. A method for inhibiting the growth of a blue-mold or a gray-mold on a pome fruit, comprising the steps of:
  a) isolating a *Sporobolomyces roseus* yeast;
  b) culturing the *Sporobolomyces roseus*;
  c) suspending the *Sporobolomyces roseus* in a medium to form a suspension having a sufficient concentration of the *Sporobolomyces roseus* to inhibit the growth of the mold on the pome fruit; and
  d) applying the suspension to the surface of the fruit in an amount sufficient to inhibit the growth of the mold on the pome fruit.

16. A method for inhibiting the growth of a blue-mold or a gray-mold on a pome fruit, comprising the steps of:
  a) isolating a *Sporobolomyces roseus* yeast;
  b) culturing the *Sporobolomyces roseus*;
  c) suspending the *Sporobolomyces roseus* in a medium to form a first suspension having a concentration of *Sporobolomyces roseus* in the range of between about $10^3$ and $10^6$ cfu per milliliter;
  d) isolating *Pseudomonas syringae* bacterium;
  e) culturing the *Pseudomonas syringae*;
  f) suspending the *Pseudomonas syringae* in a medium to form a second suspension having a concentration in the range of up to about $10^9$ cfu per milliliter of the *Pseudomonas syringae*;
  g) combining the first suspension and second suspension to form a preparation; and
  h) applying the preparation to the fruit in an amount which is sufficient to inhibit the growth of the mold on the fruit.

* * * * *